United States Patent
Cardinali et al.

(10) Patent No.: US 10,617,358 B2
(45) Date of Patent: Apr. 14, 2020

(54) PORTABLE ELECTRONIC DEVICE AS HEALTH COMPANION

(71) Applicant: Apple Inc., Cupertino, CA (US)

(72) Inventors: Steven P. Cardinali, Campbell, CA (US); William C. Lukens, San Francisco, CA (US); Katherine E. Tong, San Francisco, CA (US); Trevor J. Ness, San Francisco, CA (US)

(73) Assignee: APPLE INC., Cupertino, CA (US)

( * ) Notice: Subject to any disclaimer, the term of this patent is extended or adjusted under 35 U.S.C. 154(b) by 168 days.

(21) Appl. No.: 15/226,729

(22) Filed: Aug. 2, 2016

(65) Prior Publication Data

US 2017/0079583 A1 Mar. 23, 2017

Related U.S. Application Data

(60) Provisional application No. 62/221,253, filed on Sep. 21, 2015.

(51) Int. Cl.
*A61B 5/00* (2006.01)
*A61B 5/145* (2006.01)
(Continued)

(52) U.S. Cl.
CPC .......... *A61B 5/681* (2013.01); *A61B 5/14517* (2013.01); *A61B 5/14539* (2013.01); *A61B 5/4266* (2013.01); *A61B 5/746* (2013.01); *A61B 5/7435* (2013.01); *A61B 10/0064* (2013.01); *A61B 5/1112* (2013.01); *A61B 5/145* (2013.01);
(Continued)

(58) Field of Classification Search
CPC ....... A61B 5/681; A61B 5/4266; A61B 5/746; A61B 5/7435; A61B 5/14539; A61B 5/14517; A61B 5/1112; A61B 5/145; A61B 5/14507; A61B 5/6801; A61B 5/6802; A61B 5/6813; A61B 10/0064; A61B 5/6887; Y02A 90/26

See application file for complete search history.

(56) References Cited

U.S. PATENT DOCUMENTS

| 4,756,314 A | * | 7/1988 | Eckenhoff ............ A61B 5/4266 36/182 |
| 8,157,730 B2 | | 4/2012 | LeBoeuf et al. |

(Continued)

FOREIGN PATENT DOCUMENTS

JP 2010046196 A * 3/2010 ............... A61B 5/00

OTHER PUBLICATIONS

The English-language machine translation of the description of JP 2010-46196 (Year: 2010).*

*Primary Examiner* — Navin Natnithithadha
*Assistant Examiner* — Andrey Shostak
(74) *Attorney, Agent, or Firm* — Dorsey & Whitney LLP

(57) ABSTRACT

A wearable consumer electronic product includes at least a housing arranged to carry operational components comprising a processor and a band having a pliable band body and a securing means arranged to secure the band body to the housing. In one embodiment, the pliable band body has a size and shape suitable for wrapping around an individual appendage and that includes an opening that leads to a cavity within the band body suitable for accumulating an amount of water and a band sensor embedded within the band body in communication with the cavity.

7 Claims, 8 Drawing Sheets

(51) Int. Cl.
*A61B 10/00* (2006.01)
*A61B 5/11* (2006.01)

(52) U.S. Cl.
CPC ......... *A61B 5/14507* (2013.01); *A61B 5/6801* (2013.01); *A61B 5/6802* (2013.01); *A61B 5/6813* (2013.01); *A61B 5/6887* (2013.01); *Y02A 90/26* (2018.01)

(56) References Cited

U.S. PATENT DOCUMENTS

| | | | |
|---|---|---|---|
| 8,652,040 B2 | 2/2014 | LeBoeuf et al. | |
| 8,830,068 B2 * | 9/2014 | Campbell | A61B 5/0008 340/573.1 |
| 2007/0027383 A1 * | 2/2007 | Peyser | A61B 5/14521 600/347 |
| 2008/0146892 A1 * | 6/2008 | LeBoeuf | A61B 5/11 600/300 |
| 2010/0234711 A1 * | 9/2010 | Sugenoya | A61B 5/14521 600/365 |
| 2014/0343371 A1 | 11/2014 | Sowers, II et al. | |

* cited by examiner

B - B

PORTABLE ELECTRONIC DEVICE AS HEALTH COMPANION

CROSS-REFERENCE TO RELATED APPLICATIONS

This application claims the benefit of U.S. Provisional Application No. 62/221,253, filed on Sep. 21, 2015 and titled "PORTABLE ELECTRONIC DEVICE AS HEALTH COMPANION", which is incorporated by reference herein in its entirety.

FIELD

The following disclosure relates to an electronic device. In particular, the following disclosure relates to a wearable electronic device that can be used to determine and evaluate external environmental factors that can affect a user's health.

BACKGROUND

Electronic devices may include certain features to enhance a user experience. For example, an electronic device may include a sensing element designed to monitor the user as well as a surrounding environment. In particular, a wearable electronic device can include multiple sensors used for interacting with a user that can provide information related to a current physical condition and/or health of the user as well as provide relevant environmental information.

SUMMARY

In one aspect, a wearable consumer electronic device is described. The consumer electronic product includes a housing arranged to carry operational components. The consumer electronic product also includes an interconnected group of sensors at least one of which is carried by the housing and operable as a sensor engine in communication with the processor. The sensor engine includes a first sensor capable of detecting a threshold amount of water and a second sensor capable of detecting a property of the water, where detection of the threshold amount of water by the first sensor causes the second sensor to detect the property of the water. In one embodiment, the consumer electronic product is wearable.

A method carried out by a wearable consumer electronic product includes at least the following operations: detecting at least a threshold amount of water by a first sensor, detecting a property of the water by a second sensor in communication with the first sensor, and providing a notification in accordance with the detected property.

In another aspect, a wearable consumer electronic product includes at least a housing arranged to carry operational components comprising a processor and a band having a pliable band body and a securing mechanism arranged to secure the band body to the housing. In one embodiment, the pliable band body has a size and shape suitable for wrapping around a user's appendage and that includes an opening that leads to a cavity within the band body suitable for accommodating an amount of water, a band sensor embedded within the band body in communication with the cavity.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The disclosure will be readily understood by the following detailed description in conjunction with the accompanying drawings, wherein like reference numerals designate like structural elements, and in which.

Figure 1:
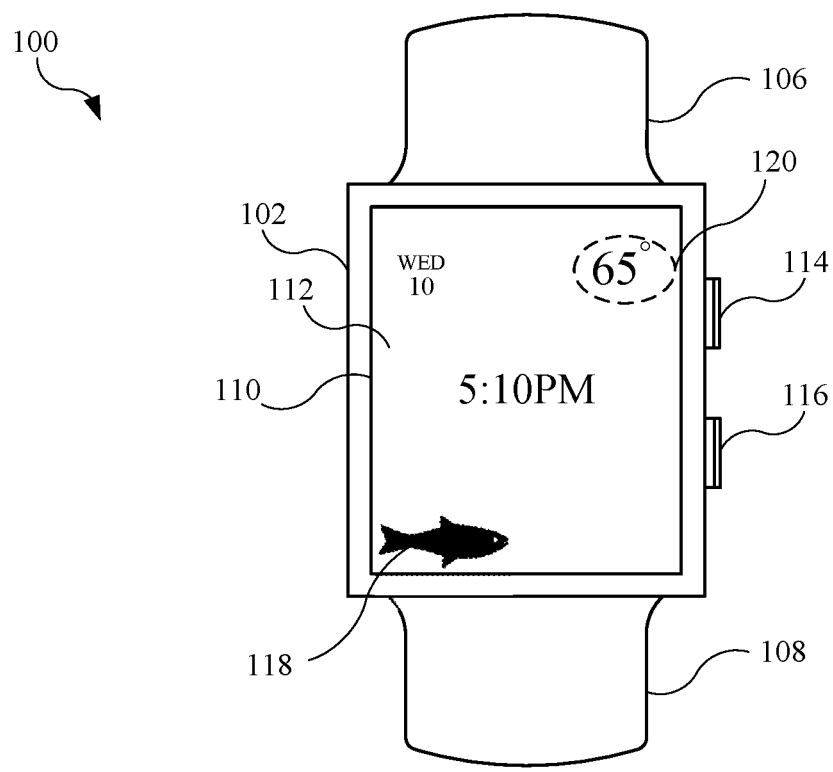
FIG. 1 shows a front view of an electronic device.

Those skilled in the art will appreciate and understand that, according to common practice, various features of the drawings discussed below are not necessarily drawn to scale, and that dimensions of various features and elements of the drawings may be expanded or reduced to more clearly illustrate the embodiments of the present invention described herein.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting such that other embodiments may be used, and changes may be made without departing from the spirit and scope of the described embodiments.

The following disclosure relates to an electronic device. In particular, the electronic device can have a form factor that renders the electronic device wearable. By wearable, it is meant that a user can wear the electronic device as a decorative (but also functional) accessory that can be secured or otherwise attached to a garment or appended to a user's limb much like a watch. In the context of this discussion, however, the electronic device can be considered an accessory that can be carried or worn by the user. In this way, the electronic device can act both as an adornment as well as a source of useful information. The information can be provided real time and can be associated with a current physical state of the user and/or information regarding an external environment that the user would find of interest. For example, the electronic device can be worn as a bracelet or a watch that can be taken along on various athletic endeavors such as rock climbing, skydiving, scuba diving, jogging etc. In this way, the electronic device can be used to monitor (and record if need be) external conditions such as temperature, pressure, light conditions, speed, distance and so on. The external conditions can be related to various physical activities that the electronic device can anticipate that the user will take part and as such may have an impact on the user's health and/or enjoyment of the physical activity.

A particularly beneficial, but by no means only, use of the electronic device is one in which the electronic device determines that a body of water is nearby and based upon an anticipated context of use, the electronic device can determine which properties of the water and/or surrounding environment would be relevant to the user and in particular the health of the user. For example, when the electronic device determines that the user wearing the electronic device has been exposed to at least a threshold amount of water (indicating that, for example, the user/electronic device is submerged or otherwise exposed to a significant body of water as opposed to a lesser amount of water associated with, for example, rain), a sensing element carried by the electronic device and/or associated with the electronic device, can be used to detect properties of the water deemed to be of interest. The detection of the specific property (or properties) can, in turn, be used to notify the user that participating in the anticipated activity may have an adverse impact on the user's current health or enjoyment and action should be taken.

For example, when the electronic device detects the threshold amount of water using a primary sensor, a secondary sensor, or sensors, can be triggered to detect specific properties of the water. A salt content sensor, for example, can determine a salt content of the water and based upon the result determine that the body of water associated with the sample of water is either a fresh water lake/pool/river, or an ocean. Once the type of water is established, other sensors can come into play specifically designed to detect properties most likely to be associated with the type of water and that could potentially have a substantial impact on the health of the user or the enjoyment of an activity by the user. For example, if the type of water is determined to be salt, a geo-location sensor can be used to determine a geo-location of the user that can be used to identify the body of water associated with the water sample. Another sensor can be designed to detect bio-matter such as dangerous pathogens that if detected can trigger a warning to avoid entering the body of water or leave the body of water if already entered. Another sensor could be used to detect chemicals in the water, and so on.

It should also be noted that the electronic device could be worn in such a way that the amount of water detected can be associated with sweat originating from the individual wearing the electronic device. Sweat is a salty, watery solution produced by sweat glands that is passed through numerous microscopic channels opening onto the skin surface that forms a protective layer often referred to as the acid mantle having a particular level of acidity characterized by pH from about 4 to 5.5 (pH is well known term that describes the overall acidity or alkalinity of an aqueous solution. For example, pure water is neutral and has a pH value of 7.0 whereas an acidic solution will have a pH value less than 7 and an alkaline solution a pH greater than 7). Accordingly, the ability to detect aspects of perspiration, or sweat, originating from the individual wearing the electronic device can provide insight into a general condition of the individual's current state of health.

The embodiments shown and described relate to an electronic device. The electronic device can take the form of a wearable electronic device that can be attached to a garment worn by a user or carried with respect to an appendage (such as a wrist) of the user. These and other embodiments are discussed below with reference to FIGS. 1-8. However, those skilled in the art will readily appreciate that the detailed description given herein with respect to these Figures is for explanatory purposes only and should not be construed as limiting.

FIG. 1 illustrates a front view of an embodiment of an electronic device 100, in accordance with the described embodiments. In some embodiments, the electronic device 100 is a mobile communication device, such as a smart phone. In other embodiments, the electronic device 100 is a wearable computing device. In the embodiment shown in FIG. 1, the electronic device 100 is a wearable electronic device designed to secure with an appendage (for example, an arm or a leg) of a user of the electronic device 100.

Electronic device 100 may include an enclosure 102 formed from a rigid material, such as a metal (including stainless steel or aluminum). The enclosure 102 may be coupled with a first band 106 and a second band 108, with the first band 106 and the second band 108 are designed to secure the electronic device 100 to an appendage of a user. Also, the electronic device 100 may include a display module 110 designed to display visual content, including a day and a time of the day. In some embodiments, the display module 110 is a light-emitting diode ("LED") display. Further, in some embodiments, the display module 110 is an organic light-emitting diode ("OLED") display. The display module 110 may further include a cover glass 112 disposed over the display module 110. In addition to displaying time, the display module 110 may also display visual content based upon applications, or "apps," stored on a memory circuit (not shown) disposed between the enclosure 102 and the display module 110. For example, icon 118 can be used to indicate a particular athletic activity whereas icon 120 can indicate current local conditions such as temperature.

The electronic device 100 may include several input features electrically coupled with one or more processors (not shown), and designed to control the display module 110. For example, as shown in FIG. 1, the electronic device 100 includes a first control input 114 and a second control input 116, each of which may be partially disposed in openings of the enclosure 102. The first control input 114 may take the form of a dial design for clockwise and counter-clockwise rotation, with the rotation used to control the display module 110. Further, the first control input 114 may be depressed to define a further control input feature. The second control input 116 may take the form of a button that provides an additional control input feature when depressed. Although not shown, the first control input 114 and/or second control input 116 may be disposed in other locations of the enclosure 102. Also, the electronic device 100 may include more or fewer control inputs in other embodiments. Further, the electronic device 100 may include a touch sensor (not shown) disposed behind (and in some cases integrated) with the display module 110. This allows the user to further control the display module 110 by depressing the cover glass 112 triggering the touch sensor to generate a control input and alter the visual content of the display module 110.

Electronic device 100 can also include a sensor or a number of interconnected sensors that are operable as a sensor engine. The sensors can be environmental sensors arranged to detect an aspect of an environment. By interconnected it is meant that individual sensors can be in communication with each other directly or indirectly via another component, such as a processor. In an embodiment, some of the interconnected sensors can be carried by enclosure 102 whereas other sensors can be carried by band 106 or 108. Regardless of their locations, the sensors can provide information that can be used to evaluate specific properties of an aspect of the local environment and determine an overall potential impact on a user's health or enjoyment of a current or anticipated activity of the user. For example, if a sensor 132 on band 108 detects a sample of water corresponding to at least a threshold amount of water (indicating that the user is submerged in a body of water), this information can be used to trigger or otherwise cause another sensor to detect a particular property of that sample water, such as salinity. This information can be sent to a processor, for example, that can then trigger other sensors to operate to detect specific water properties that taken together can form a health impact profile corresponding to an anticipated health impact and provide a notification accordingly.

Figure 2:
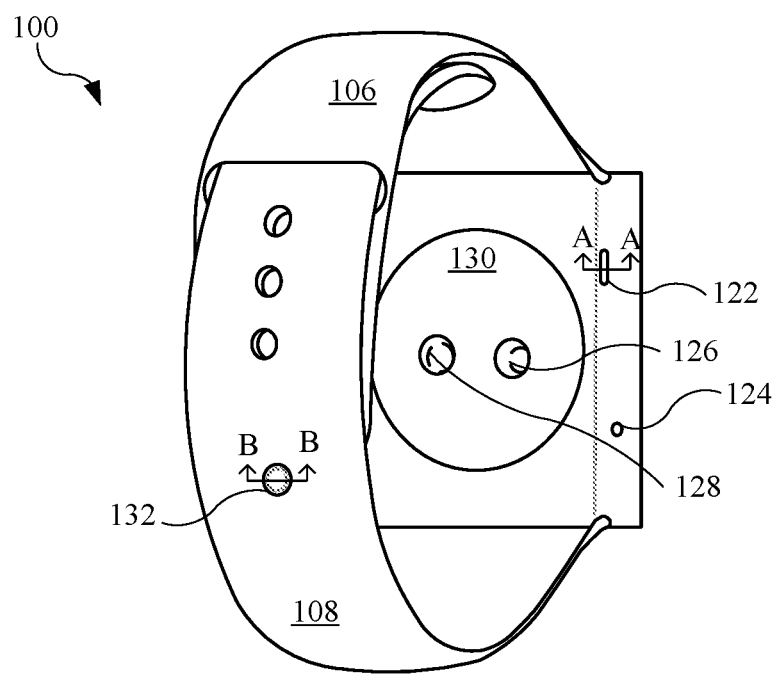
FIG. 2 shows a rear view of electronic device shown in FIG. 1.

For example, FIG. 2 shows a rear view of electronic device 100 shown in FIG. 1 illustrating several openings in enclosure 102. For example, electronic device 100 may include a first opening 122 in the enclosure 102 that may allow, for example, sampling by a sensor1 of the external environment for the presence of, for example, ambient water. For example, the sensor engine can include a water sensor used to detect a presence of at least a threshold amount of water indicating that electronic device 100 is, for example, either partially or fully submerged by a body of water (in contrast to being exposed rain droplets as an example). Also, the electronic device 100 may include a second opening 124 in the enclosure 102 that may allow, for example, sampling of another specimen of the water by sensor2 for properties of the water. Although the first opening 122 and the second opening 124 are shown in distinct locations, the first opening 122 and the second opening 124 may vary in location along the enclosure 102, and further, may vary in size and shape. Further, the number of openings may vary according to the functionality of the electronic device 100 as well as the number of sensors associated with the sensor engine. For example, an additional opening (not shown) may be used in conjunction with the first opening 122 to enhance an amount of the water sampled or provide additional inputs such as an air sample.

The electronic device 100 shown in FIG. 2 may include additional features that can be used to detect not just environment factors but factors associated with the user. This information can be used to determine a context in which the electronic device is being used. For example, if the user sensor detects that an elevated heart rate and/or body temperature, the context of use can be that of running or exercising. For example, the electronic device 100 may include a light source 126 designed to emit light in the form of light pulses. In some embodiments, the light source 126 includes a light-emitting diode ("LED"). Further, in some embodiments, the light source 126 includes a generally green color. Also, the electronic device 100 may include a sensing element 128 (that can also be part of the sensor engine) designed to sense light from the light source 126 that is reflected by, for example, a user wearing the electronic device 100. Accordingly, in some embodiments, the sensing element 128 is a photoelectric sensor or photodiode. Although a single light source and a single sensing element are shown, other embodiments may include two or more light sources as well as two or more sensing elements. In other embodiments, sensor 128 can be used to detect an amount of perspiration, or sweat, on the surface of the user's skin. In this way, sensor 128 can be used to trigger other sensors that can determine, for example, a pH level of the sweat, a presence of pathogens, chemicals associated with diseases, and so forth. Also, a cover 130, formed from a material such as glass or crystal, may overlay the light source 126 and the sensing element 128, with the cover 130 being transparent in locations corresponding to the light source 126 and the sensing element 128.

Figure 3A:
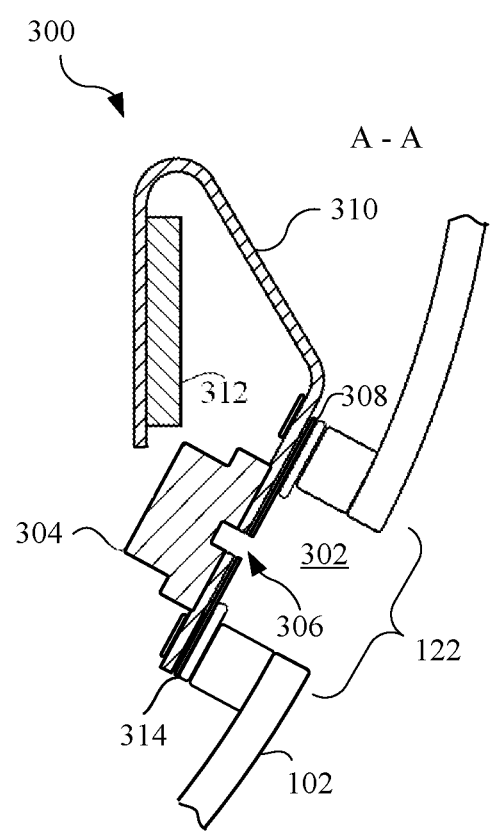
FIG. 3A shows representative cross sectional view of a sensor carried by an electronic device in accordance with the described embodiments.

FIG. 3A shows representative cross sectional view of sensor system 300 in accordance with the described embodiments. It should be noted housing 102 of electronic device 100 could carry that sensor system 300. As discussed above with respect to FIG. 1, housing 102 can include opening 122 that can lead to cavity 302, or well, having volume V that defines at least a threshold amount of water indicating that electronic device 100 is submerged or otherwise in contact with a substantial amount of water corresponding to a lake, stream, pool, ocean, and so forth. It should be noted that the orientation of opening 122 towards a rear portion of electronic device 100 allows that during normal use, opening 122 is unlikely be in position such that water droplets associated with rain, lawn sprinklers, etc. can cross opening 122 such that the threshold amount of water will accumulate within cavity 302. In this way, false alerts or triggers can be avoided. Sensor 304 can be positioned to receive a sample of water that has accumulated in cavity 302 by way of sensor port 306 that corresponds to an opening in membrane 308. In one embodiment, membrane 308 is water impermeable whereas in other embodiments, membrane 308 allows at least some water to pass from cavity 302 to sensor 304. Flex 310 can be used to carry a detection signal from sensor 304 to circuitry 312. Circuitry 312 can take the form of another sensor, a processor, or any other appropriate electronic device. In order to prevent leaks, seals 314 can be placed between membrane 308 and supports 316.

Figure 3B:
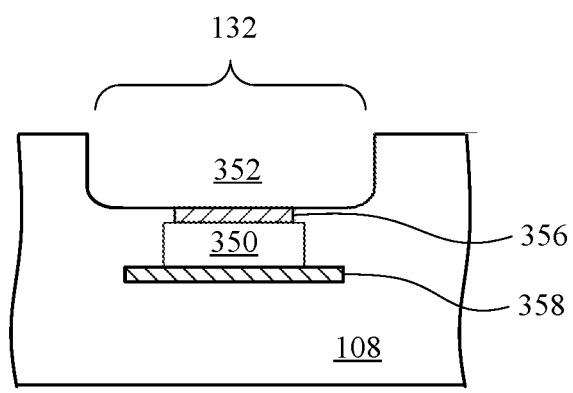
FIG. 3B shows representative cross section of band carried sensor in accordance with the described embodiments.

FIG. 3B shows representative cross section along line B-B of FIG. 2 of band carried sensor 350 in accordance with the described embodiments. Sensor 350 can be carried by band 106 and/or band 108. Accordingly, sensor 350 can communicate with cavity 352 formed in band body 354. Cavity 352 can accommodate a threshold amount of water that can be the same or different than that used to trigger sensor 300. In one embodiment, membrane 356 can provide a transport path for water accumulated in cavity 352 to sensor 350. Sensor 350 can be connected to external circuitry by way of flex 358 configured to move with bending and torsional movements of band body 106 or 108.

Figure 4:
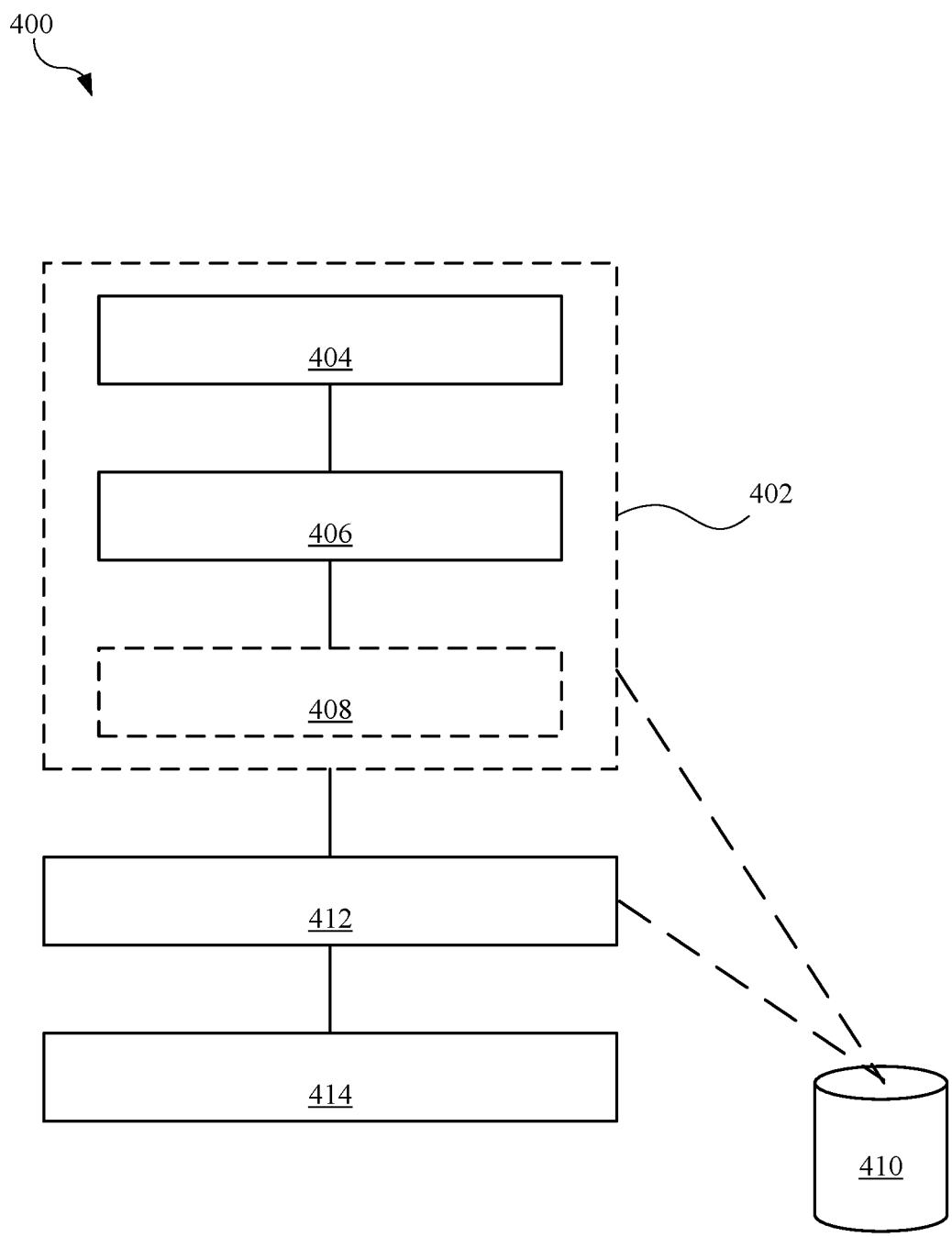
FIG. 4 shows a system in accordance with the described embodiments.

FIG. 4 shows system 400 in accordance with the described embodiments. System 400 can include sensor engine 402 that can include primary sensing layer 404 that can be used as a triggering mechanism for sensor engine 402. By triggering mechanism it is meant that primary sensing layer 404 can be used to periodically monitor an external environment for a particular element of the external environment. More specifically, primary sensing layer 404 can determine that a threshold amount of the environmental element is present and if so can then trigger secondary sensing layer 406 arranged to detect a particular property of the environmental element. In some cases, tertiary sensing layer 408 can be used to detect other aspects of the environmental element based upon the activity of secondary sensing layer 406. In any case, sensor engine 402 can be in communication with data store 410 well suited for storing data accumulated by sensor engine 402. Processing layer 412 can provide processing resources that can be used to analyze relevant data provided by sensor engine 402 or retrieved from data store 410. Based upon the processing carried out by processing layer 412, notification layer 414 can provide a notification in accordance with a pre-determined set of conditions or observations provided by sensor engine 402. The notification can be related to aspects of the environmental element that a user can consider important or at least relevant to a health of the user. The notification can provide a warning or other suggestions of a course of action based upon current environmental conditions. In some embodiments, the notification can be based upon a current context of use of system 400. For example, if the context of use is that system 400 is part of a wearable computing system attached to a user that is currently swimming, the notification can indicate dangerous conditions such as rip tides or if system 400 is in communication with an external circuit (through a wireless connection, for example) the notification can provide a warning of dangerous predators such as sharks are in the area.

Figure 5:
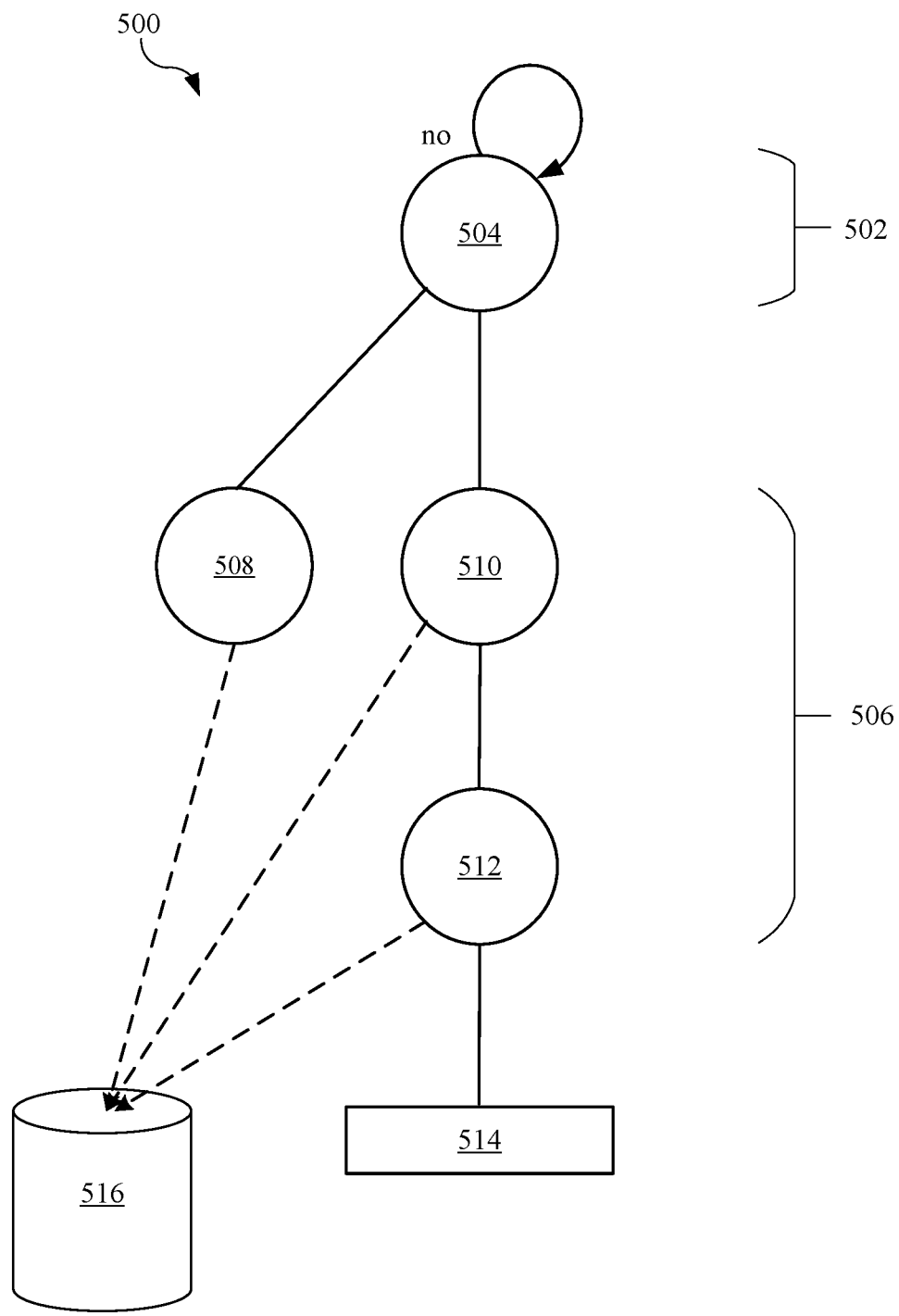
FIG. 5 shows a particular implementation of a system as a water sensing system in accordance with the described embodiments.

FIG. 5 shows a particular implementation of system 400 as water sensing system 500 in accordance with the described embodiments. Water sensing system 500 can include water detection layer 502 arranged to periodically monitor an external environment for water. More specifically, water detector 504 can periodically monitor for at least a threshold amount of water being present. When water detector 504 determines that the threshold amount of water is present, then some or all of secondary sensors in property detection layer 506 are triggered. The secondary sensors can be configured to detect a particular property of the water such as, for example, salt content, pH, temperature, etc. In some cases, a context of use can be used to further refine the types and numbers of secondary sensors called into action. For example, if a geo-location device indicates that system 500 is near a particular body of water, when water detector 504 detects the threshold amount of water, then selected ones of property detection layer 506 can be triggered that are dedicated to detect particular properties of water in that area. If geo-location data indicates that body of water is near a lake, then bio-matter sensor 508 arranged to detect bio-matter such as harmful pathogens and chemical sensor 510 for detecting harmful chemicals can be triggered. In some cases, additional sensors referred to as tertiary sensor 512 can be used to detect still further properties of the water. In any case, a processor can analyze sensor data and cause notification level 514 to provide a notification that can be used to inform a user of any pertinent information based upon the analysis performed by water sensing system 500. It should be noted that data store 516 could be used to store relevant data.

Figure 6:
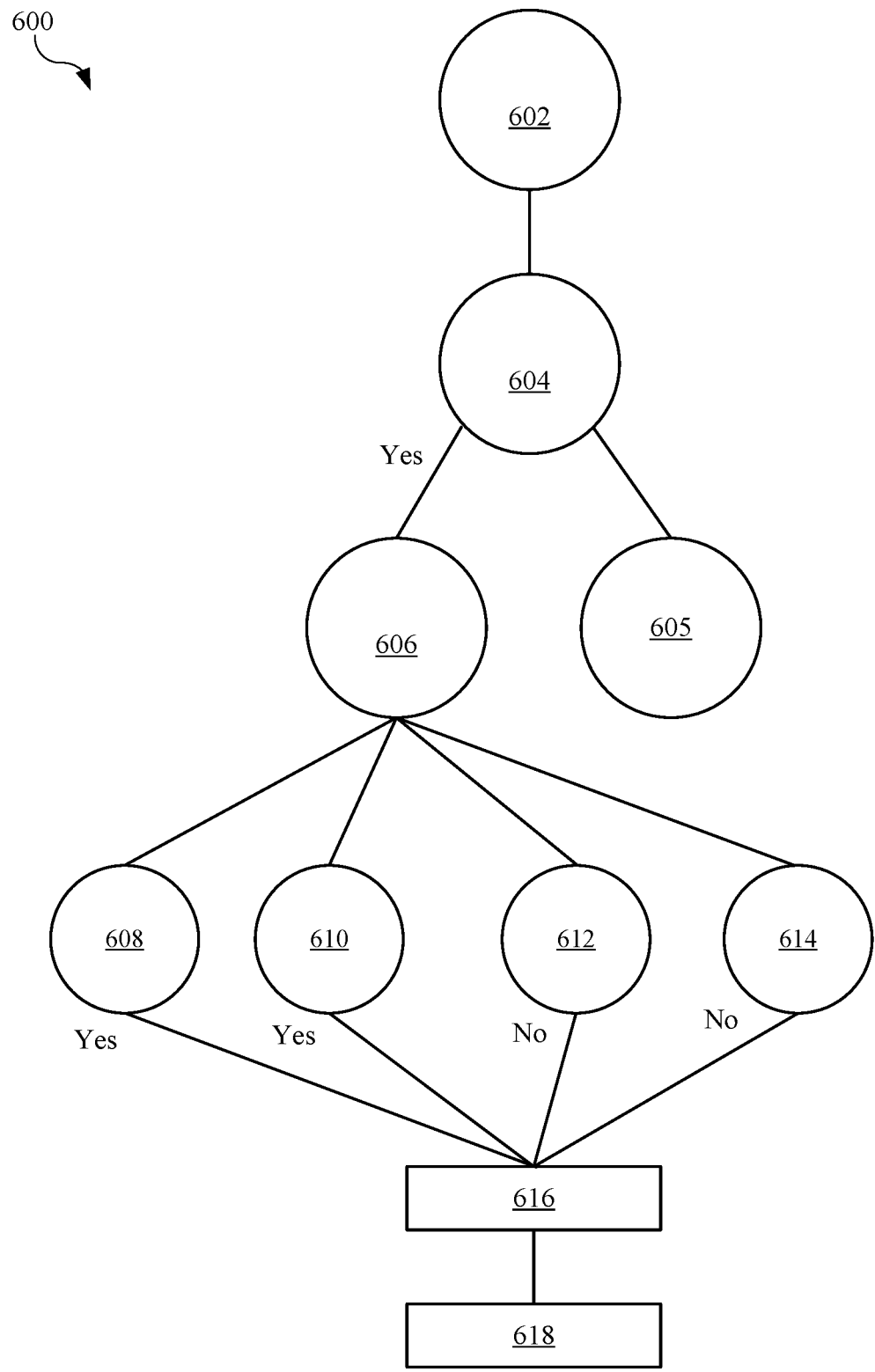
FIG. 6 shows a particular example of a system in accordance with the described embodiments.

FIG. 6 shows system 600 in accordance with the described embodiments. For example, when a threshold amount of water is detected by water detector 602, then salinity detector 604 can be used to determine the salinity of the water and based upon that result, a determination can be made that the water is either salt water or fresh water. If the water is determined to correspond to salt water, then a geo-location device can fix a current location as being an ocean 606 (or a lake). The location can also be indirectly determined by a context of use evaluation as well as data received from the user in the form of user physical data (heartbeat, breathing rate, etc.) In this case, certain other sensors can be called upon to detect particular properties of the salt water associated with the ocean and more particularly to the location at which system 600 is positioned. The other sensors can be selected to determine an overall view of how benign the current environment is with regards to a user's health. For example, bio-matter sensor 608 can be used to detect pathogens and pH sensor 610 can be used to detect unsafe pH levels. Moreover, other sensors such as chemical sensor 612 can be used to detect dangerous chemicals whereas particulate sensor 614 can be used to detect particulates. In any case, information from the sensors can be processed by processor 616 that can cause notification layer 618 to issue a relevant notification. For example, a notification can be issued indicating that bio-matter and unsafe pH levels are detected (denoted by "YES") whereas there is no need to trigger notification for chemicals or particulates (denoted by "NO").

Figure 7:
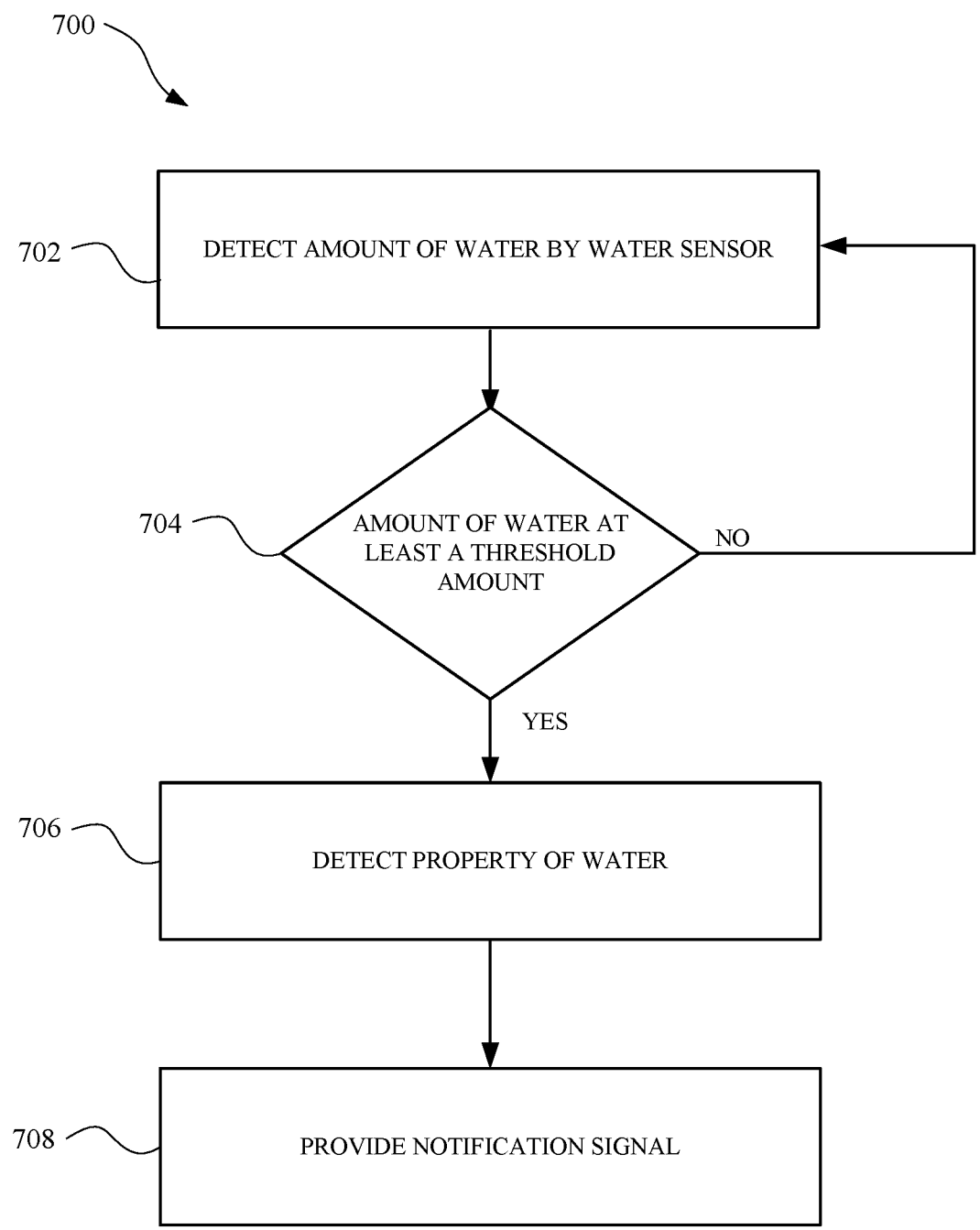
FIG. 7 illustrates a flowchart showing a method for using a wearable electronic device as an environmental sensor/health monitor in accordance with the described embodiments.

FIG. 7 illustrates a flowchart 700 showing a method for using a wearable electronic device as an environmental sensor/health monitor in accordance with the described embodiments. Process 700 can be carried out by detecting an amount of water at 702. At 704, a determination is made whether or not the amount of water is at least a threshold amount. If it is determined that the amount of water is at least the threshold amount, then a property of the water is detected at 706 and a notification is issued at 708.

Figure 8:
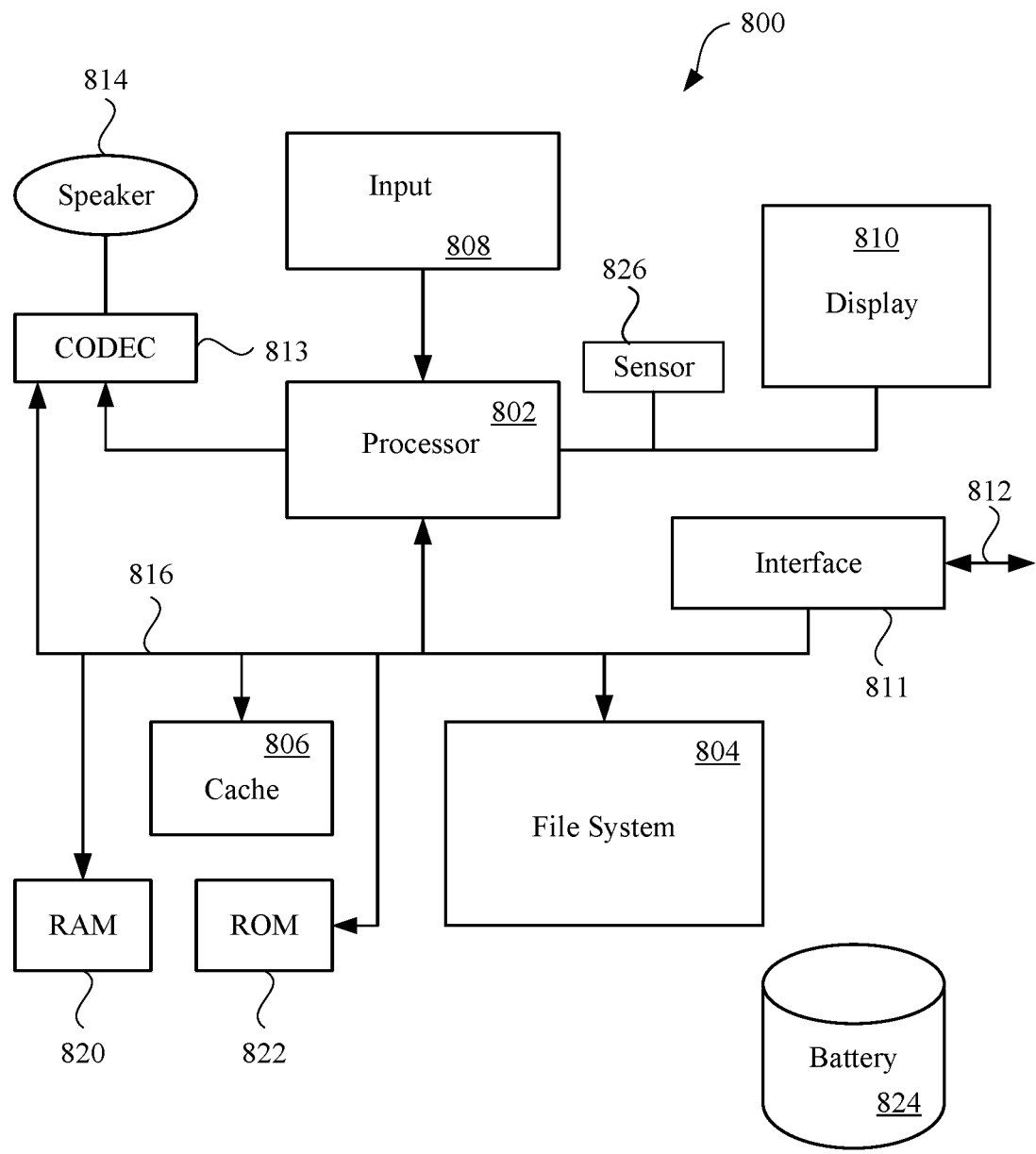
FIG. 8 is a block diagram of an electronic device suitable for use with the described embodiments.

FIG. 8 is a block diagram of an electronic device 800 suitable for use with the described embodiments. The electronic device 800 illustrates circuitry of a representative computing device. The electronic device 800 includes a processor 802 that pertains to a microprocessor or controller for controlling the overall operation of the electronic device 800. The electronic device 800 stores media data pertaining to media items in a file system 804 and a cache 806. The file system 804 is, typically, a semiconductor memory, cloud storage, or storage disks or hard drives. The file system 804 typically provides high capacity storage capability for the electronic device 800. However, since the access time to the file system 804 is relatively slow, the electronic device 800 can also include a cache 806. The cache 806 is, for example, Random-Access Memory (RAM) provided by semiconductor memory. The relative access time to the cache 806 is substantially shorter than for the file system 804. However, the cache 806 does not have the large storage capacity of the file system 804. Further, the file system 804, when active, consumes more power than does the cache 806. The power consumption is often a concern when the electronic device 800 is a portable media device that is powered by a battery 824. The electronic device 800 can also include a RAM 820 and a Read-Only Memory (ROM) 822. The ROM 822 can store programs, utilities or processes to be executed in a non-volatile manner. The RAM 820 provides volatile data storage, such as for the cache 806.

The electronic device 800 also includes a user input device 808 that allows a user of the electronic device 800 to interact with the electronic device 800. For example, the user input device 808 can take a variety of forms, such as a button, keypad, dial, touch screen, audio input interface, visual/image capture input interface, input in the form of sensor data, etc. Still further, the electronic device 800 includes a display 810 (screen display) that can be controlled by the processor 802 to display information to the user. A data bus 816 can facilitate data transfer between at least the file system 804, the cache 806, the processor 802, and the CODEC 813.

In one embodiment, the electronic device 800 serves to store a plurality of media items (e.g., songs, podcasts, etc.) in the file system 804. When a user desires to have the electronic device play a particular media item, a list of available media items is displayed on the display 810. Then, using the user input device 808, a user can select one of the available media items. The processor 802, upon receiving a selection of a particular media item, supplies the media data (e.g., audio file) for the particular media item to a coder/decoder (CODEC) 813. The CODEC 813 then produces analog output signals for a speaker 814. The speaker 814 can be a speaker internal to the electronic device 800 or external to the electronic device 800. For example, headphones or earphones that connect to the electronic device 800 would be considered an external speaker.

The electronic device 800 also includes a network/bus interface 811 that couples to a data link 812. The data link 812 allows the electronic device 800 to couple to a host computer or to accessory devices. The data link 812 can be provided over a wired connection or a wireless connection. In the case of a wireless connection, the network/bus interface 811 can include a wireless transceiver. The media items (media assets) can pertain to one or more different types of media content. In one embodiment, the media items are audio tracks (e.g., songs, audio books, and podcasts). In another embodiment, the media items are images (e.g., photos). However, in other embodiments, the media items can be any combination of audio, graphical or visual content. Sensor 826 can take the form of circuitry for detecting any number of stimuli. For example, sensor 826 can include a Hall Effect sensor responsive to external magnetic field, an audio sensor, a light sensor such as a photometer, and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A wearable electronic device, comprising:
    a housing at least partially defining an internal volume, a cavity in communication with the internal volume, and an opening that leads from an ambient environment to the cavity;
    a water impermeable membrane disposed between the internal volume and the cavity, the water impermeable membrane defining a sensor port; and
    a sensor engine, the sensor engine comprising:
        a first sensor to detect an amount of water in the cavity above a threshold, the first sensor disposed in the internal volume and in communication with the cavity through the sensor port: and
        a second sensor to detect a property of the water in the cavity when the first sensor detects the amount of the water above the threshold; and
        a processor in communication with the sensor engine, the processor programmed to identify a type of the water based at least in part on the detected property and to instruct the wearable electronic device to perform an action based at least in part on the identified type.

2. The wearable electronic device as recited in claim 1, further comprising:
    a band coupled to the housing and arranged to secure the housing to a user.

3. The wearable electronic device as recited in claim 2, wherein the second sensor is carried by the housing.

4. The wearable electronic device as recited in claim 2, wherein one of the first sensor or the second sensor is carried by the housing and the other of the first sensor or the second sensor is carried by the band.

5. The wearable electronic device as recited in claim 1, wherein the property is selected from a group that includes a pH level of the water, a salinity of the water, a biological content of the water, a particulate level of the water, a chemical content of the water, and a temperature of the water.

6. The wearable electronic device as recited in claim 1, wherein the sensor engine further comprises a third sensor and the action comprises activating the third sensor.

7. The wearable electronic device as recited in claim 1, wherein the action comprises at least one of providing a notification to a user, activating one or more sensors of the wearable electronic device, or recording one or more external conditions.

* * * * *